United States Patent
Thomas

(10) Patent No.: US 6,635,667 B2
(45) Date of Patent: Oct. 21, 2003

(54) METHODS OF TREATMENT USING MAO-A AND MAO-B INHIBITORS SUCH AS L-DEPRENYL

(76) Inventor: Thomas N. Thomas, 3457 Shoreline Cir., Palm Harbour, FL (US) 34684

( * ) Notice: Subject to any disclaimer, the term of this patent is extended or adjusted under 35 U.S.C. 154(b) by 0 days.

(21) Appl. No.: 10/137,342

(22) Filed: May 3, 2002

(65) Prior Publication Data

US 2002/0128299 A1 Sep. 12, 2002

Related U.S. Application Data

(60) Division of application No. 09/881,199, filed on Jul. 27, 2000, now Pat. No. 6,432,991, which is a continuation-in-part of application No. PCT/US99/01670, filed on Jan. 26, 1999.
(60) Provisional application No. 60/072,718, filed on Jan. 27, 1998.

(51) Int. Cl.[7] .............................................. A61K 31/435
(52) U.S. Cl. ........................ 514/365; 514/617; 514/652; 514/655
(58) Field of Search ................................. 514/365, 617, 514/652, 655

(56) References Cited

U.S. PATENT DOCUMENTS

| | | | | | |
|---|---|---|---|---|---|
| 4,906,668 A | * | 3/1990 | May et al. | ................... | 514/706 |
| 5,981,598 A | * | 11/1999 | Tatton | ......................... | 514/649 |
| 6,063,805 A | * | 5/2000 | Oxenkrug et al. | .......... | 514/415 |

OTHER PUBLICATIONS

Thomas, Neuroreport, vol. 91(11), pp. 2595–2600 (1998).*
Thomas, *Neuroreport,* vol. 91(11), pp. 2595–2600, 1998.

* cited by examiner

*Primary Examiner*—James H Reamer
(74) *Attorney, Agent, or Firm*—Foley & Lardner

(57) ABSTRACT

Effects of MAO-A or MAO-B inhibitors such as L-deprenyl on both cerebral and peripheral vasculature, on non-vascular smooth muscle, on the nervous system, and on platelets, RBC, WBC, mast cells, macrophages, and glial cells are disclosed. The effects are the result of a mode of action for MAO-A or MAO-B inhibitors such as L-deprenyl which is totally unrelated to selective inhibition of MAO-A and/or MAO-B. Therapeutic methods of using MAO-A or MAO-B inhibitors such as L-deprenyl to treat a variety of disorders are disclosed.

12 Claims, No Drawings

METHODS OF TREATMENT USING MAO-A AND MAO-B INHIBITORS SUCH AS L-DEPRENYL

This application is a division of Ser. No. 09/881,199, now U.S. Pat. No. 6,432,991 which is a CIP of application No. PCT/US99/01670, filed Jan. 26, 1999 provisional application No. 60/072,718, filed Jan. 27, 1998.

BACKGROUND OF THE INVENTION

This invention relates to methods of treatment using MAO-A or MAO-B inhibitors such as L-deprenyl.

L-Deprenyl, also known as selegiline or Eldepryl, is a selective inhibitor of mitochondrial monoamine oxidase type B (MAO-B). It belongs to a class of enzyme-activated irreversible inhibitors also described as "suicide" inhibitors, because the compound acts as a substrate for monoamine oxidase, the action of which on the compound results in irreversible inhibition. L-Deprenyl forms a monovalent complex with monoamine oxidase as an initial, reversible step. Subsequent interaction of L-deprenyl with MAO leads to a reduction of the enzyme-bound flavine-adenine dinucleotide (FAD), and concomitant oxidation of the inhibitor. The oxidized inhibitor then reacts with FAD at the N-5-position in a covalent manner.

L-Deprenyl has been used clinically as an MAO-B inhibitor in combination with levo-dopa (L-dopa) to treat Parkinson's disease. L-Dopa treatment alone is optimally effective only for the first few years of therapy. The anti-Parkinson's disease action of L-deprenyl was based on the theory that MAO-B was the predominant form of MAO in the brain and that brain MAO rather than peripheral enzyme activity was to be selectively inactivated. Use of L-deprenyl in conjunction with L-dopa therapy enhances dopaminergic transmission. This permits a lowering of the dosage of L-dopa, which prolongs the effect of L-dopa and decreases adverse side effects of L-dopa.

L-Deprenyl has been reported to enhance catecholaminergic activity and diminish serotoninergic activity in the brain, by mechanisms unrelated to MAO-B inhibition. In rats it has been shown to reduce brain damage after exposure to transient hypoxia-ischemia, the proposed mechanism being either a prevention of the rise of $H_2O_2$ or an increase in enzymatic radical scavenging capacity, particularly by facilitating superoxide dismutase activity. Indeed, some of these additional mechanisms may contribute to L-deprenyl's mode of action in Parkinson's disease.

SUMMARY OF THE INVENTION

It is an object of the present invention to provide a method of increasing nitric oxide production.

It is a further object of the present invention to provide a method of treating diseases of brain and blood vessels related to a deficiency in nitric oxide production.

It is yet another object of the present invention to provide a method of protecting the vascular endothelium.

It is a further object of the present invention to provide a method of relaxing non-vascular smooth muscle.

It is another object of the present invention to provide a method of treating neuronal disorders.

It is a further object of the present invention to provide a method of treating cellular disorders of platelets, RBC, WBC, mast cells, macrophages, and glial cells.

These and other objects of the invention are provided by a method of treating a disorder of the vasculature, comprising administering to a subject suffering from such a disorder an effective amount of an MAO-A or MAO-B inhibitor. The disorder of the vasculature may be a disorder of the cerebral or peripheral vasculature. Specific vasculature disorders which can be treated include essential, renovascular, pulmonary, and ocular hypertension, myocardial infarction, and cerebrovascular stroke.

The disorder of the vasculature may be associated with a deficiency in NO production, with the MAO-A or MAO-B inhibitor exerting an endothelium-dependent effect on the vasculature. Alternatively, the disorder may be a disorder of the vasculature associated with a toxic effect of β-amyloid on the vasculature, in which case the MAO-A or MAO-B inhibitor protects the endothelium of the vasculature from P-amyloid. The disorder also may be one not associated with a deficiency in NO production, in which case the MAO-A or MAO-B inhibitor exerts an endothelium-independent effect on the vasculature.

The present invention also provides a method of treating a neuronal disorder other than Parkinson's Disease or Alzheimer's Disease, comprising administering to a subject suffering from such a disorder an effective amount of an MAO-A or MAO-B inhibitor. The disorder may be associated with a deficiency in NO production, in which case the MAO-A or MAO-B inhibitor stimulates production of NO. Alternatively, the neuronal disorder may be caused by a toxic effect of β-amyloid on neurons.

Also provided according to the invention is a method of treating a disorder of the non-vascular smooth muscle, comprising administering to a subject suffering from such a disorder an effective amount of an MAO-A or MAO-B inhibitor. Disorders of the non-vascular smooth muscle that can be treated include airway obstruction or another respiratory disorder and a gastrointestinal motility disorder.

The present invention also provides a method of treating a cellular disorder of platelets, RBC, WBC, mast cells, macrophages, or glial cells, comprising administering to a subject suffering from such a disorder an effective amount of an MAO-A or MAO-B inhibitor. In a preferred embodiment, the MAO-A or MAO-B inhibitor acts as an anti-platelet agent or an anti-inflammatory agent.

In preferred embodiments, the MAO-A or MAO-B inhibitor is selected from the group consisting of L-deprenyl, clorgyline, pargyline, N-(2-aminoethyl)-4-chlorobenzamide hydrochloride, N-(2-aminoethyl)-5(3-fluorophenyl)-4-thiazolecarboxamide hydrochloride, and derivatives thereof. A dose of 1–100 mg/day, preferably 1–10 mg/day, of the MAO-A or MAO-B inhibitor is used in accordance with the present invention.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

It has been discovered, surprisingly, that MAO-A or MAO-B inhibitors such as L-deprenyl display many modes of action which are totally unrelated to their mode of action as selective inhibitors of MAO-A and/or MAO-B. For example, it has been found that MAO-A or MAO-B inhibitors such as L-deprenyl exert effects on both cerebral and peripheral vasculature, some of which are mediated by nitric oxide (NO) and others of which are NO-independent. More particularly, MAO-A or MAO-B inhibitors such as L-deprenyl have been found to stimulate NO production rapidly and stereospecifically when administered in vitro or in vivo to peripheral or cerebral blood vessels. They also have been found to blunt the vasoconstriction caused by a number of vasoconstrictors.

For example, L-deprenyl at low doses ($\leq 10$ $\mu$M) causes a rapid NO-mediated endothelium-dependent vasodilation. At higher doses L-deprenyl produces a slow progressive NO—and endothelium-independent direct relaxation of vascular smooth muscle. The NO-mediated, endothelial-dependent effects of L-deprenyl and other MAO-A or MAO-B inhibitors on the cerebral and peripheral vasculature makes them useful in treating a variety of disorders, including essential, renovascular and pulmonary hypertension, glaucoma (by reduction of intraocular pressure), macular degeneration, and erectile impotence all of which result from a significant reduction of endothelium-dependent relaxation. The NO-mediated, endothelial-dependent effects also are useful in preserving organs for transplantation. The blood-brain barrier is composed of endothelial cells, and by protecting the endothelium L-deprenyl and other MAO-A or MAO-B inhibitors protect the integrity of the blood-brain barrier. They also are useful in cases of myocardial infarction and cerebrovascular stroke which result from an alteration of endothelial function. The endothelium-independent direct relaxation of vascular smooth muscle by MAO-A or MAO-B inhibitors such as L-deprenyl can be a useful adjunct in treatment of these disorders.

MAO-A or MAO-B inhibitors such as L-deprenyl also have been discovered to exert a potent relaxant effect on non-vascular smooth muscle, which is mediated both by guanylate cyclase and cyclic GMP-independent mechanisms. This action makes them useful for treating disorders associated with relaxation of smooth muscle, such as airway obstruction and other respiratory disorders, gastrointestinal motility disorders, hemorrhoids, sphincter and smooth muscle spasm in the gastrointestinal tract, and bladder dysfunction. They may be used to counteract premature labor and to relax the birth canal during delivery. They also are useful in relaxing the urinary tract for the passage of kidney stones, and may be used to alleviate smooth muscle contraction and spasm, thus facilitating diagnostic procedures such as endoscopy, bronchoscopy, laparoscopy, cystoscopy and catheterization.

It additionally has been found that L-deprenyl and other MAO-A or MAO-B inhibitors exert NO-mediated effects on the nervous system that are unrelated to their action on MAO-A or MAO-B, leading to their use in treatment of neuronal disorders other than Parkinson's Disease. Neuronal disorders caused by a deficiency in NO production include age-related neurodegenerative diseases, as well as other memory disorders. Exemplary of disorders that can be treated effectively with L-deprenyl and other MAO-A or MAO-B inhibitors are Alzheimer's disease, Down's syndrome, amyotrophic lateral sclerosis (ALS), Huntington's disease, AIDs dementia, brain trauma, and learning and movement disorders. The compounds also can be used in neuron protection.

Finally, it has been discovered that MAO-A or MAO-B inhibitors such as L-deprenyl affect a diverse group of cells other than endothelial, non-vascular smooth muscle and neuronal cells. These include both NO-mediated and NO-independent effects on platelets, RBC, WBC, mast cells, macrophages, and glial cells. Most notable in this context are their use as anti-platelet agents or as anti-inflammatory agents. Examples of treatable disorders include asthma and thrombosis.

Thus, MAO-A or MAO-B inhibitors such as L-deprenyl can be used to effect both NO-mediated and NO-independent actions on the cerebral and peripheral vasculature, on non-vascular smooth muscle, and on a diverse group of other cells. They also are useful in treating neuronal tissues, including brain tissue, which suffer from a deficiency in NO production.

Activity has been demonstrated for a wide variety of MAO-A and MAO-B inhibitors, including L-deprenyl, clorgyline, pargyline, RO-16-6491 (N-(2-aminoethyl)4-chlorobenzamide hydrochloride), and RO-41-1049 (N-(2-aminoethyl)-5-(3-fluorophenyl)4-thiazolecarboxamide hydro-chloride). Each of these compounds has been shown to have the ability to inhibit contraction, to dilate blood vessels, to inhibit $\beta$-amyloid and to stimulate NO production in the brain. Derivatives of these compounds may be used, as well as other MAO-A and MAO-B inhibitors and derivatives thereof. Exemplary of compounds that are structurally related to L-deprenyl are N-propargylamine compounds, N-methyl-propargylamine and N-methyL-N-(2-pentyl)-propargylamine can be used in place of L-deprenyl.

The effect of these compounds on vasodilation has been confirmed in both peripheral and cerebral blood vessels. Low concentrations of the compounds produce relaxation of aortic rings with intact endothelium. This effect is not detectable in endothelium-free tissue and is greatly diminished in endothelium-intact tissue treated with the nitric oxide synthase (NOS) inhibitor L-Nitro-Arginine-Methyl-Ester, (L-NAME), which exhibits an enhanced vasoconstriction. Thus the vasodilatory effect of low concentrations of the compounds appears to be mediated by endothelial NOS.

Further evidence of the NO-mediated, endothelium-dependent vasodilatory effect of these compounds is demonstrated by the fact that pretreatment with freshly prepared hemoglobin blocks the vasodilatory effect of low concentrations of the compounds in rat aorta and bovine cerebral artery. By binding NO, hemoglobin prevents the vasodilatory action of NO. The endothelium-dependent effect of the compounds also is prevented by methylene blue ($10^{-4}$ M). Methylene blue is an inhibitor of the enzyme guanylate cyclase which catalyzes the formation of cyclic GMP, which in turn mediates the vasodilatory effect of NO in vascular smooth muscle.

NO or a labile NO-containing compound is considered to be the endothelium-derived relaxing factor (EDRF), which plays a vital role in the regulation of vascular tone. However, the endothelial-mediated vasodilation induced by MAO-A or MAO-B inhibitors such as L-deprenyl appears not to be mediated by any of the classical endothelial receptors. It is present even when different vasoconstrictors are used, e.g. phenylephrine, norephrine, 5-HT, the prostaglandin agonist U46619, or K+. The vasodilatory effect also appears not to be mediated by cholinergic receptors on endothelium since the antagonist atropine ($10^{-4}$ M) does not abolish the vasodilatory effect of L-deprenyl and other MAO-A or MAO-B inhibitors. Nor is the effect prostaglandin-mediated, since the cyclooxygenase inhibitor indomethacin ($10^{-5}$ M) fails to antagonize L-deprenyl-mediated vasodilation. The phospholipase A2 inhibitor manolide (10–5 M) also has no detectable effect on L-deprenyl-mediated vasodilation.

The possibility of amphetamine metabolites mediating the action of L-deprenyl can be eliminated. The D-isomer is metabolized to D-amphetamine which has 10 times the amphetamine potency of the L-amphetamine derived from L-deprenyl, yet the D-isomer is of much lower potency than the L-isomer.

High concentrations of L-deprenyl and other MAO-A and MAO-B inhibitor, e.g., >2.5×10$^{-5}$ M for L-deprenyl, cause a slowly developing relaxation in endothelium-denuded aorta. This effect is not reversed by L-NAME, demonstrating that high concentrations of L-deprenyl directly relax vascular smooth muscle through an NO-independent mechanism as opposed to the NO-mediated, endothelium-dependent relaxation caused by low concentrations of the drug.

Rat and bovine cerebral vessels show a vasodilatory effect similar to that shown by aortic rings. Cerebral arteries with intact endothelium show a rapid vasodilatory response to low doses of L-deprenyl and other MAO-A and MAO-B, e.g., ≦10 μM for L-deprenyl, which is prevented by L-NAME. As in peripheral blood vessels, in endothelium-denuded cerebral arteries higher doses of L-deprenyl and other MAO-A and MAO-B inhibitors induce a slow progressive relaxation which is not reversed by L-NAME.

The direct vasodilatory effect of L-deprenyl and other MAO-A or MAO-B inhibitors on vascular smooth muscle has similarities to the activation of calcium-dependent potassium channels and is probably mediated through ion channels. Both the endothelium-dependent and independent vasodilatory effects of L-deprenyl are abolished in calcium-free medium. The constitutive form of the enzyme NO synthase present in endothelial cells and neurons requires calcium for activation. Thus, the generation of NO by L-deprenyl and other MAO-A or MAO-B inhibitors involves the activation of constitutive NO synthase.

Antagonism of vasoconstriction by L-deprenyl extends to antagonism of vasoconstriction caused by a number of vasoconstrictors, as demonstrated by its action on isolated segments of blood vessels maintained in tissue bath. Rat aortic rings with intact endothelium, when pretreated with L-deprenyl or other MAO-A or MAO-B inhibitors, exhibit a dose-dependent decrease in contraction in response to the vasoconstrictor PE. Contractions at lower doses of PE are more sensitive to the effect of the compounds. Surprisingly, D-deprenyl actually enhances vasoconstriction, demonstrating the superior ability and stereospecific action of L-deprenyl in antagonizing PE-induced contraction.

Pretreatment of the intact aortic rings with the NOS inhibitor L-NAME abolishes the inhibitory action of L-deprenyl and other MAO-A and MAO-B inhibitors on PE-induced contraction. The inactive isomer D-Nitro-Arginine-Methyl-Ester (D-NAME) is less effective in blocking the effect of L-deprenyl. L-Deprenyl displays a similar inhibition of vasoconstriction induced by serotonin in bovine mid-cerebral artery. Inhibition of vasoconstriction by 10$^{-4}$ M L-deprenyl also is observed in endothelium-denuded peripheral and cerebral arteries.

The vascular effects of L-deprenyl and other MAO-A or MAO-B inhibitors have been confirmed in vivo. Aortas removed from rats one hour following injection with L-deprenyl or another MAO-A or MAO-B inhibitors or saline show diminished vasoconstriction in response to the vasoconstrictor PE and enhanced vasodilatory response to the vasodilator acetylcholine. The enhanced response to acetylcholine is evident from an observed increased response to low concentrations of acetylcholine as compared to control rats treated with saline. The results indicate that the effect of L-deprenyl and other MAO-A or MAO-B inhibitors on the vasculature persist for a significant period of time.

The discovery of the previously unknown effects of L-deprenyl and other MAO-A or MAO-B inhibitors on the endothelium, particularly the low-dose NO-mediated effects, leads directly to a method of protecting the endothelium from β-amyloid toxicity. The present inventor has demonstrated that β-amyloid causes endothelial dysfunction. Damaged endothelium exhibits an enhanced response to vasoconstrictors and diminished sensitivity to vasodilators. This includes enhanced vasoconstriction with serotonin and diminished relaxation to the endothelium-dependent vasodilators acetylcholine and bradykinin. Amyloid-mediated vascular damage is postulated to be an early event relative to development of Alzheimer's Disease. Administration of L-deprenyl and other MAO-A or MAO-B inhibitors can prevent the vascular damage caused by β-amyloid, thereby delaying the progression of Alzheimer's Disease. Administration of compounds according to the invention also is effective in combating amyloid angiopathy.

The ability of L-deprenyl and other MAO-A or MAO-B inhibitors to prevent vascular damage caused by β-amyloid has been confirmed by studies with rat aorta with the β-amyloid peptide primarily associated with cerebrovascular deposits in Alzheimer's disease, and the major circulating form of amyloid. β-amyloid produces a significant increase in vasoconstriction induced by PE in rat aorta, and a diminished relaxation response to acetylcholine. Both effects are antagonized by pretreatment with L-deprenyl and other MAO-A or MAO-B inhibitors. Moreover, the aortas from rats injected with L-deprenyl and other MAO-A or MAO-B inhibitors do not exhibit any of the typical features of β-amyloid-mediated endothelial dysfunction.

L-Deprenyl and other MA-O-A or MAO-B inhibitors also antagonize the effect of β-amyloid in bovine mid-cerebral arteries. β-amyloid produces significantly increased vasoconstriction in response to serotonin, which is completely blocked by pretreatment with L-deprenyl and other MAO-A or MAO-B inhibitors. L-Deprenyl and other MAO-A or MAO-B inhibitors also antagonize the diminished vasodilatory response of the cerebral artery induced by β-amyloid.

It is postulated that the cytoprotective effect of L-deprenyl and other MAO-A or MAO-B inhibitors is mediated by increased NO production, but it may be due in part to oxygen free radical scavenging by the compounds. Regardless of the mechanism, the ability of the compounds to antagonize β-amyloid-mediated endothelial dysfunction in peripheral and cerebral blood vessels provides a significant treatment for preventing the vascular damage caused by β-amyloid, particularly in Alzheimer's Disease.

In addition to its effects on vascular and non-vascular smooth muscle, including those involving β-amyloid, NO mediates a wide range of physiological activities, particularly certain forms of learning and memory. NO has a role in the cellular basis of memory by facilitating long-term potentiation (LTP). During LTP induction in the CA1 region of the hippocampus, NO generated in the dendrites of pyramidal cells transmits retrograde signals from the postsynaptic to the presynaptic terminals. The endothelial isoform of NOS seems to be the major enzyme involved in the maintenance of LTP in the hippocampus. NO also is involved in neuron protection.

NO mediates some of the effects of glutamate/NMDA receptor pathway on neuronal functioning and synaptic plasticity. L-Deprenyl and other MAO-A or MAO-B inhibitors stimulate NO production in all brain regions examined as well as in the mid-cerebral artery. L-Deprenyl is a particularly potent stimulant of NO production, being more effective in rat brains than the endogenous NOS stimulant L-glutamate: in all brain regions except the hippocampus, L-deprenyl stimulates NO at a more than 100-fold lower concentration than L-glutamate. In bovine cerebellum both 10 and 100 mM L-deprenyl produce significantly more NO than 1 mM L-glutamate, and concentrations as low as 1 mM have a stimulatory effect on NO production. In each case, D-deprenyl has considerably less activity.

L-Deprenyl and other MAO-A and MAO-B inhibitors can be administered orally in capsule form. For example, a recommended regimen for administration in accordance with the present invention is 1–100 mg/day, preferably divided among two or more doses. A preferred dosage is 10–20 mg/day.

The following examples illustrate various actions of L-deprenyl according to the present invention, but do not limit the scope of the invention in any way. Further aspects and variations of the invention, based on the disclosure above and the following examples, will be apparent to the person of ordinary skill in the art. In addition, the contents of the following articles are incorporated by reference herein in their entirety, and provide illustrations of various aspects of the invention:

Price et al., Neurological Research, 19:1 (1997)
Thomas et al., J. Cardiovascular Pharm. 30: 1 (1997)
Sutton et al, Exp. Cell Res. 230: 368 (1997)
Thomas, Neurobiology, 21:343 (2000)
Thomas et al., Neuroreport, 9:2595–2600 (1998)
Thomas et al., Alzheimer's Disease and Related Disorders, p. 493–500, 1999.

EXAMPLE 1
Effect of L-deprenyl on phenylephrine-induced vasoconstriction of peripheral arteries Freshly isolated rat aorta or bovine brains were placed in ice-cold Kreb's buffer solution. The thoracic aorta or mid-cerebral artery was carefully excised and sectioned into ring segments of 3 mm in length. These segments were mounted on hooks, attached to force displacement transducers and equilibrated under the optimum tension of 2.0 g in a 5 ml tissue bath containing oxygenated (5% CO2 in O2) Kreb's bicarbonate buffer at 37° C.

After incubation for 60 minutes the viability of the blood vessel with intact endothelium was established by stimulating contraction of the aorta or cerebral vessel with phenylephrine (PE) ($5 \times 10^{-8}$ M) or serotonin (5-HT) ($5 \times 10^{-10}$ M), respectively, and relaxation with the endothelium-dependent vasodilators acetylcholine or bradykinin. The blood vessel preparations were then rinsed and equilibrated for 15 minutes before repeating each series of contraction/relaxations.

For each set of experiments, the endothelium was removed mechanically from two or more tissues and the absence of endothelium was confirmed by testing for diminished relaxation to acetylcholine or bradykinin according to Thomas et al., Nature, 380:168–171 (1996) and Thomas et al., NeuroReport., 8:1387–1391 (1997), the contents of which are incorporated by reference herein in their entirety.

In a first experiment, blood vessel segments were constricted in a dose-dependent manner using PE (1, 2, 4 and $8 \times 10^{-8}$ M), in the presence or absence of various concentrations of L-deprenyl (10, 50 and $100 \times 10^{-6}$ M) which were added 5 minutes prior to constriction with PE. The effect of L-deprenyl was more pronounced at lower concentrations of the vasoconstrictor. Constriction in the presence of higher doses of L-deprenyl was significantly different from control contractions in the absence of the drug. Repeated measures of the analysis of variance indicated a significant interaction (PE dose by condition, p=0.0002).

In a second experiment, aortic rings were constricted by increasing concentrations of PE (2, 4, 8 and $16 \times 10^{-8}$ M), alone or following a 5 minute incubation with L-deprenyl ($10^{-4}$ M) or D-deprenyl ($10^{-4}$ M). L-Deprenyl significantly reduced vasoconstriction, while the biologically inactive isomer D-deprenyl had a detectable stimulatory effect on the contraction. Repeated measures of the analysis of variance indicated a significant interaction (acetylcholine dose by condition, p=0.0002).

In a third experiment, vessels were constricted by varying doses of PE (2, 4, 8 and $16 \times 10^{-8}$ M), alone or following a 5 minute incubation with L-deprenyl ($10^{-4}$ M), D-NAME ($10^{-4}$ M) plus L-deprenyl ($10^{-4}$ M), or L-NAME ($10^{-4}$ M) plus L-deprenyl ($10^{-4}$ M). L-Deprenyl significantly diminished PE-induced vasoconstriction. Pretreatment with L-NAME nearly abolished the L-deprenyl effect. The inactive isomer D-NAME was considerably less effective in blocking the L-deprenyl effect. Repeated measures of the analysis of variance indicated a significant interaction (PE dose by condition, p=0.0002).

(In the foregoing experiments, all chemicals and reagents were purchased from Sigma Chemical Co. (St. Louis, Mo., U.S.A.). All drugs, agonists/antagonists and enzyme inhibitors were obtained from Research Biochemicals International, (Boston, Mass., U.S.A.).

EXAMPLE 2
Direct Vasodilatory Effect of L-deprenyl on phenlephrine-induced Vasoconstriction of Peripheral Arteries Thoracic rat aorta and bovine mid-cerebral arteries with intact or mechanically-denuded endothelium were preconstricted submaximally and then relaxed with increasing doses of L-deprenyl ($0.1-400 \times 10^{-3}$ M), alone or following preincubation with various antagonists, or enzyme inhibitors.

In a first experiment, rat aortas with intact or mechanically-denuded endothelium were preconstricted with PE ($5 \times 10^{-8}$ M), alone or following a 15 minute incubation with L-NAME ($10^{-4}$ M), and then relaxed with increasing doses of L-deprenyl. Untreated aortic rings with intact endothelium showed a relaxation response to doses as low as 5 mM of L-Deprenyl. Pretreatment with L-NAME enhanced the contraction response to PE, and higher doses of L-deprenyl were required to produce a small vasodilatory effect. Removal of the endothelium produced an enhanced response to PE, and no vasodilation was observed at the low doses of L-deprenyl.

In a second experiment, aortic rings with intact or denuded endothelium were preconstricted with PE ($5 \times 10^{-8}$ M) as previously described and then relaxed with increasing doses of L-deprenyl. In aortic rings with viable endothelium, low doses of L-deprenyl produced a rapid vasodilation. In tissue denuded of endothelium low doses (<10 mM) were ineffective, whereas higher doses elicited a slow vasodilatory action. Addition of L-NAME ($10^{-4}$ M) following the addition of the highest dose of L-deprenyl did not reverse the vasodilation.

In a third experiment, bovine mid-cerebral arteries with intact endothelium were constricted with 5-HT ($5 \times 10^{-10}$ M). The endothelium-denuded tissue was contracted with 60% of the 5-HT in order to equalize the contractions. The cerebral arteries were relaxed with increasing doses of L-deprenyl. In healthy vessels with intact endothelium, low doses ($\leq 10$ mM) were capable of eliciting a rapid vasodilatory response while high doses relaxed the vessel nearly to basal levels. Endothelium-free tissue demonstrated only minor vasodilatory response to low doses, whereas higher doses produced a slow gradual relaxation. Addition of L-NAME ($10^{-4}$ M) did not reverse the vasodilatory effect of high doses of L-deprenyl.

EXAMPLE 3
In vivo Vascular Effect of L-deprenyl

Adult male Sprague-Dawley rats weighing 200–250 gm (n=4 per group) were injected intraperitoneally with 10 mg/kg body weight of freshly prepared L-deprenyl in saline. Control animals were injected with saline alone. After 1 hour the animals were sacrificed and the aortas isolated and sectioned as described above.

In a first experiment, aortic rings from control or L-deprenyl-injected animals were preconstricted submaximally with PE ($5\times10^{-8}$ M) and then relaxed with the endothelium-dependent vasodilator acetylcholine ($10^{-5}$ M). Aorta from L-deprenyl-injected rats showed diminished vasoconstriction in response to PE and enhanced vasodilatory response to the vasodilator acetylcholine.

In a second experiment, aortic segments were constricted with PE ($5\times10^{-8}$ M) and then relaxed with increasing doses of acetylcholine ($10^{-8}$ M $10^{-5}$ M). Enhanced response to acetylcholine in the L-deprenyl-injected animal was evident from an increased response to low concentrations of acetylcholine. Cumulative relaxation values for aorta from L-deprenyl-injected animals were significantly greater than control values. Repeated measures of the analysis of variance indicated a significant interaction (acetylcholine dose by condition, p=0.0002).

EXAMPLE 4
Attenuation of Amyloid-$\beta$-induced Vascular Dysfunction by L-deprenyl A first experiment demonstrated inhibition of $\beta$-amyloid-induced enhancement of vasoconstriction by L-deprenyl in rat aorta. Aortic rings with intact or mechanically-denuded endothelium were constricted submaximally using PE ($5\times10^{-8}$ M), alone or following a 5 minute incubation with L-deprenyl ($10^{-4}$ M) or D-deprenyl ($10^{-4}$ M), or L-deprenyl plus amyloid $\beta$ ($10^{-6}$ M) for 15 minutes. L-deprenyl was added 5 minutes before amyloid $\beta$. Percentage of PE-induced contraction under control conditions was calculated. Pretreatment of intact vessels with $\beta$-amyloid (1 mM) caused a significant increase in vasoconstrictor response to PE. Addition of L-deprenyl (100 mM) 5 minutes prior to the introduction of $\beta$-amyloid abolished this enhancement effect. D-Deprenyl had no significant effect on vasoconstriction.

A second experiment demonstrated inhibition of $\beta$-amyloidinduced attenuation of endothelium-dependent vasodilation by L-deprenyl. Aortic segments were preconstricted with PE ($5\ 10^{-8}$ M) and then relaxed with increasing doses of the endothelium-dependent vasodilator acetylcholine ($10^{-8}$ M–$10^{-5}$ M) under control conditions and following a 15 minute incubation with amyloid $\beta$ ($10^{-6}$ M) or L-deprenyl ($10^{-4}$ M) plus $\beta$-amyloid ($10^{-6}$ M). Percentage decrease in tension of PE-induced contraction under control conditions was calculated. Pretreatment of intact aorta with $\beta$-amyloid (1 mM) caused attenuation of dose-dependent response to the endothelium-dependent vasodilator acetylcholine. Pretreatment of the vessel with L-deprenyl (100 mM) 5 minutes prior to the addition of $\beta$-amyloid preserved the relaxation response to acetylcholine. Cumulative relaxation values following $\beta$-amyloid treatment were statistically different from control values. Relaxation responses following L-deprenyl plus $\beta$-amyloid treatment were not significantly different from control values. Repeated measures of the analysis of variance indicated a significant interaction (acetylcholine dose by condition, p=0.0002).

A third experiment demonstrated inhibition of $\beta$-amyloid-mediated enhancement of vasoconstriction by L-deprenyl in bovine mid-cerebral arteries. Bovine mid-cerebral arteries with intact or mechanically-denuded endothelium were constricted submaximally using 5-HT ($5\times10^{-10}$ M), alone or following a 5 minute incubation with L-deprenyl ($10^{-4}$ M) or D-deprenyl ($10^{-4}$ M), or L-deprenyl+amyloid $\beta$ ($10^{-6}$ M). Percentage of 5-HT-induced contraction under control conditions were calculated. L-Deprenyl antagonized the $\beta$-amyloid-induced enhancement of contraction in cerebral vessels. L-Deprenyl also prevented the diminished vasodilatory response to the vasodilator bradykinin in cerebral arteries treated with $\beta$-amyloid.

EXAMPLE 5
Stimulation of Nitric Oxide Production by L-deprenyl

Freshly isolated rat and/or bovine brains were placed in ice-chilled Kreb's buffer solution. Following dissection of the cerebellum, cortex, and hippocampus, the brain regions were minced, and weighed into glass tubes. Brain tissue from various regions or segments of isolated midcerebral artery were incubated for 30 minutes at 37° C. in 2.5 ml of oxygenated Kreb's buffer solution (5% $CO_2$ in $O2$; pH 7.4). The buffer was removed and replaced with fresh buffer. The tissue was re-equilibrated for an additional 10 minutes in buffer alone prior to the addition of various agonists/stimulants. Following a 30 minute incubation in the presence or absence of test compounds, 0.5 ml aliquots of the incubation medium were removed and placed on ice for subsequent nitrite analysis.

Nitric oxide was quantified by measuring accumulation of nitrites. Levels of nitrite were analyzed spectrophotometrically using a modification of the Griess assay for nitrites, as described in Cook et al., *Analyt. Biochem.* 238: 150–158 (1996). To each sample was added 0.5 ml of sulfanilic acid (1%) freshly prepared in 1 N HCl. Following a 30 second reaction time, 0.5 ml of N-(1-napthyl)ethylenediamine (NEDA) (1% in ddH2O) was added. Samples were allowed to react with color reagents for an additional 5 minutes at room temperature. Aliquots (200 ml) were then transferred directly to a microplate for nitrite analysis. Absorbance at 548 nm was measured spectrophotometrically using a UV-VIS microplate-reader. The concentrations of nitrite in the samples (nM/mg of tissue) were calculated from the absorbance values in comparison to linear standard curves for nitrite which were obtained simultaneously.

Brain tissue from various regions or segments of isolated mid-cerebral artery were incubated for 30 minutes at 37° C., alone or in the presence of L-glutamate ($10^{-3}$ M), L-deprenyl (1.0, 5.0, 10.0 or $100\times10^{-6}$ M), or D-deprenyl ($10^{-5}$ M or $10^{-4}$ M).

L-Deprenyl produced NO in a dose dependent manner, and generated considerably more NO than either the clinically-inactive isomer D-deprenyl or the endogenous activator L-glutamate. L-Deprenyl was capable of producing considerable amounts of NO at a concentration (10 mM) that was 100-fold lower than that of L-glutamate (1 mM). Comparison of NO production by L-glutamate (1 mM) or L-deprenyl (10 mM) in bovine cerebellum, frontal cortex, hippocampus and middle cerebral arteries revealed that L-deprenyl produced significantly more NO than L-glutamate at concentrations 100-fold lower than L-glutamate in the cerebellum and cortex. L-Deprenyl stimulated NO production in all brain regions examined as well as mid-cerebral arteries.

EXAMPLE 6
Effect of L-deprenyl on Dilation of Trachea

Freshly isolated tracheas from guinea pigs were placed in ice-cold Kreb's buffer solution. The tracheas were sectioned into ring segments of approximately 3 mm in length. These segments were mounted on hooks, attached to force displacement transducers and equilibrated under the optimum tension of 2.0 g in a 5 ml tissue bath containing oxygenated (5% CO2 in O2) Kreb's bicarbonate buffer at 37° C. Segments were pretreated with L-NAME (10 $\mu$M).

Pretreated trachea segments were constricted using $10^{-7}$ acetylcholine. The tissue was then relaxed with increasing concentrations of L-deprenyl, $1\times10^{-7}$ M, $1\times10^{-6}$ M, $5\times10^{-6}$ M, $1\times10^{-5}$ M, $5\times10^{-5}$ M, $1\times10^{-4}$ M, and $2\times10^{-4}$ M, which were added 7, 9, 11, 13, 15, 23 and 31 minutes, respectively, after administration of acetylcholine. L-deprenyl produces significant relaxation of the trachea.

EXAMPLE 7
Effect of L-deprenyl on U46619-Induced Vasoconstriction of Peripheral Arteries Freshly isolated porcine kidneys were placed in ice-cold Kreb's buffer solution. The renal arteries were carefully excised and sectioned into ring segments of 3 mm in length. These segments were mounted on hooks, attached to force displacement transducers and equilibrated under the optimum tension of 2.0 g in a 5 ml tissue bath containing oxygenated (5% CO2 in $O_2$) Kreb's bicarbonate buffer at 37° C.

After incubation for 60 minutes the viability of the blood vessel with intact endothelium was established by stimulating contraction of the artery with phenylephrine (PE) ($5\times10^{-8}$ M) or serotonin (5-HT) ($5\times10^{-10}$ M), respectively, and relaxation with the endothelium-dependent vasodilators acetylcholine or bradykinin. The blood vessel preparations were then rinsed and equilibrated for 15 minutes.

Segments were pretreated with L-NAME (10 $\mu$M). Pretreated renal artery segments were constricted using U-46619 ten minutes after the pretreatment with L-NAME. The tissue was then relaxed with increasing concentrations of L-deprenyl, $1\times10^{-7}$ M, $1\times10^{-6}$ M, $5\times10^{-6}$ M, $1\times10^{-5}$ M, $5\times10^{-5}$ M, $1\times10^{-4}$ M, and $2\times10^{-4}$ M, which were added 8, 10, 11, 14, 16, 19, 22 and 36 minutes, respectively, after administration of U-46619. L-deprenyl completely relaxed the renal artery.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

What is claimed is:

1. A method of treating a neuronal disorder other than Parkinson's Disease or Alzheimer's Disease, comprising administering to a subject suffering from such a disorder an effective amount of an MAO-A or MAO-B inhibitor.

2. A method according to claim 1, wherein said MAO-A or MAO-B inhibitor is selected from the group consisting of L-deprenyl, clorgyline, pargyline, N-(2-aminoethyl)-4-chlorobenzamide hydro-chloride, N-(2-aminoethyl)-5-(3-fluorophenyl)-4-thiazolecarboxamide hydrochloride, and derivatives thereof.

3. A method according to claim 2, wherein said disorder is associated with a deficiency in NO production and said MAO-A or MAO-B inhibitor stimulates production of NO.

4. A method according to claim 2, wherein said neuronal disorder is caused by a toxic effect of β-amyloid on neurons.

5. A method of treating a disorder of the non-vascular smooth muscle, comprising administering to a subject suffering from such a disorder an effective amount of an MAO-A or MAO-B inhibitor.

6. A method according to claim 5, wherein said MAO-A or MAO-B inhibitor is selected from the group consisting of L-deprenyl, clorgyline, pargyline, N-(2-aminoethyl)-4-chlorobenzamide hydro-chloride, N-(2-aminoethyl)-5-(3-fluorophenyl)-4-thiazolecarboxamide hydro-chloride, and derivatives thereof.

7. A method according to claim 5, wherein said disorder is airway obstruction or another respiratory disorder.

8. A method according to claim 5, wherein said disorder is a gastrointestinal motility disorder.

9. A method of treating a cellular disorder of platelets, RBC, WBC, mast cells, macrophages, or glial cells, comprising administering to a subject suffering from such a disorder an effective amount of an MAO-A or MAO-B inhibitor.

10. A method according to claim 9, wherein said MAO-A or MAO-B inhibitor is selected from the group consisting of L-deprenyl, clorgyline, pargyline, N-(2-aminoethyl)-4-chlorobenzamide hydro-chloride, N-(2-aminoethyl)-5-(3-fluorophenyl)-4-thiazolecarboxamide hydrochloride, and derivatives thereof.

11. A method according to claim 10, wherein said MAO-A or MAO-B inhibitor acts as an anti-platelet agent or an anti-inflammatory agent.

12. A method according to claim 1, wherein said subject is administered from 1–100 mg/day of said MAO-A or MAO-B inhibitor.

* * * * *